US010534082B2

(12) United States Patent
Clark et al.

(10) Patent No.: US 10,534,082 B2
(45) Date of Patent: Jan. 14, 2020

(54) ACCESSIBILITY OF VIRTUAL ENVIRONMENTS VIA ECHOLOCATION

(71) Applicant: International Business Machines Corporation, Armonk, NY (US)

(72) Inventors: Adam T. Clark, Mantorville, MN (US); Jeffrey K. Huebert, Rochester, MN (US); Aspen L. Payton, Byron, MN (US); John E. Petri, St. Charles, MN (US)

(73) Assignee: International Business Machines Corporation, Amonk, NY (US)

( * ) Notice: Subject to any disclaimer, the term of this patent is extended or adjusted under 35 U.S.C. 154(b) by 0 days.

(21) Appl. No.: 15/939,505

(22) Filed: Mar. 29, 2018

(65) Prior Publication Data

US 2019/0302255 A1   Oct. 3, 2019

(51) Int. Cl.
| | |
|---|---|
| *H04R 25/00* | (2006.01) |
| *G01S 15/89* | (2006.01) |
| *G06T 19/00* | (2011.01) |
| *A61F 9/08* | (2006.01) |
| *A61H 3/06* | (2006.01) |
| *G06T 19/20* | (2011.01) |

(52) U.S. Cl.
CPC ............... *G01S 15/89* (2013.01); *A61F 9/08* (2013.01); *A61H 3/061* (2013.01); *G06T 19/003* (2013.01); *G06T 19/20* (2013.01)

(58) Field of Classification Search
None
See application file for complete search history.

(56) References Cited

U.S. PATENT DOCUMENTS

| | | | |
|---|---|---|---|
| 6,961,458 B2 * | 11/2005 | Dutta ...................... | G06T 15/00 340/4.12 |
| 8,271,888 B2 | 9/2012 | Carter et al. | |
| 8,944,923 B2 | 2/2015 | Harp et al. | |
| 9,942,701 B2 * | 4/2018 | Mappus, IV ............ | H04W 4/02 |
| 2003/0007648 A1 * | 1/2003 | Currell ..................... | H04S 7/30 381/61 |

(Continued)

OTHER PUBLICATIONS

"Devil's Tuning Fork", DePaul Game Elites (A Part of the Game Development program at DePaul University's College of Computing & Digital Media), accessed online Feb. 9, 2017, 1 page.

(Continued)

*Primary Examiner* — Quoc D Tran
(74) *Attorney, Agent, or Firm* — Stephen J. Walder, Jr.; Richard A. Wilhelm

(57) ABSTRACT

Mechanisms are provided to implement an echolocation functionality within a virtual environment. The mechanisms receive graphical information for a virtual environment, and analyzes the graphical information to detect a virtual object present in the virtual environment. One or more characteristics of the detected virtual object are identified, which may include a relative location of the virtual object to a virtual representation of a user in the virtual environment. Echo data is generated that defines characteristics of an audio output that represents the virtual object in a manner emulating an echo of a sound emitted from the virtual representation of the user in the virtual environment. Output of the audio output by the one or more audio output devices is controlled based on the generated echo data.

20 Claims, 4 Drawing Sheets

(56) References Cited

U.S. PATENT DOCUMENTS

| | | | |
|---|---|---|---|
| 2004/0241623 A1 | 12/2004 | Lenay et al. | |
| 2005/0164787 A1 | 7/2005 | Connelly | |
| 2009/0287490 A1 | 11/2009 | Cragun et al. | |
| 2010/0192110 A1* | 7/2010 | Carter | G06F 3/011 715/865 |
| 2012/0075202 A1 | 3/2012 | Michaelis | |
| 2012/0315988 A1 | 12/2012 | Tsuchida et al. | |
| 2015/0063610 A1* | 3/2015 | Mossner | H04S 5/005 381/307 |
| 2015/0264502 A1 | 9/2015 | Aoki et al. | |
| 2016/0057558 A1 | 2/2016 | Gleim | |
| 2016/0067617 A1 | 3/2016 | Tolk et al. | |
| 2018/0310116 A1* | 10/2018 | Arteaga | H04S 7/304 |
| 2019/0070064 A1* | 3/2019 | Hogle | A61H 3/061 |

OTHER PUBLICATIONS

"Edge detection", Wikipedia, accessed online Feb. 9, 2017, 9 pages.

"Is it possible to mimic echolocation in videogames?", Reddit, accessed online Feb. 9, 2017, 3 pages.

"Lurking", Digipen Institute of Technology Singapore, 2014, 2 pages.

"Perception: Navigating a Game World With Echolocation", IGN.com, accessed online Feb. 9, 2017, 10 pages.

"Virtual Environments for People Who Are Visually Impaired Integrated into an Orientation and Mobility Program", Journal of Visual Impairment & Blindness, Abstract, accessed online Dec. 14, 2016, 3 pages.

"Virtual Reality Interactive Environments for the Blind", De Montfort University, Leicester, United Kingdom, accessed online Dec. 14, 2016, 2 pages.

Brennan, Claire , "Video-less 3D games developed for blind players", BBC News, Technology, Aug. 19, 2014, 4 pages.

Ghali, Neveen I. et al., "Virtual Reality Technology for Blind and Visual Impaired People: Reviews and Recent Advances", Advances in Robotics & Virtual Reality, ISRL 26, 2012, pp. 363-385.

Huang, Ying Y., "Design and Evaluation of 3D Multimodal Virtual Environments for Visually Impaired People", Doctoral Thesis in Human-Computer Interaction, KTH, Stockholm, Sweden, 2010, 86 pages.

Lahav, O. et al., "A Virtual Environment for People Who Are Blind—A Usability Study", National Institute of Health, J Assist Technol. 2012, 6(1), Dec. 16, 2013, 21 pages.

Lahav, Orly et al., "Virtual Environments for People Who Are Visually Impaired Integrated into an Orientation and Mobility Program", Journal of Visual Impairment & Blindness, Jan. Feb. 2015, pp. 5-16.

Langille, Jane, "Echolocation Helps Blind People Navigate Everyday Life", janelangille.com, Active Living, Hearing, Published Samples, Research, Sep. 28, 2012, 8 pages.

Maidenbaum, Shachar et al., "Increasing Accessibility to the Blind of Virtual Environments, Using a Virtual Mobility Aid Based on the "EyeCane": Feasibility Study", PMC US Natinal Library of Medicine National Institutes of Health, PLoS ONE, Aug. 19, 2013, vol. 8, Issue 8, pp. 1-7.

Rush, Amanda, "Accessible device for visually impaired navigation within a virtual environment", Independence Science, Sep. 14, 2016, 3 pages.

Sohl-Dickstein, Jascha et al., "A device for human ultrasonic echolocation", University of California at Berkeley, The Redwood Center for Theoretical Neuroscience, Apr. 20, 2014, pp. 1-7.

White, Gareth R. et al., "Toward Accessible 3D Virtual Environments for the Blind and Visually Impaired", DIMEA '08, Sep. 10-12, 2008, 8 pages.

Yikra, Bob, "Virtual reality study shows echolocation in humans not just about the ears", Phys.org, http://phys.org/news/2014-11-virtual-reality-echolocation-humans-ears.html, Nov. 12, 2014, 3 pages.

* cited by examiner

ACCESSIBILITY OF VIRTUAL ENVIRONMENTS VIA ECHOLOCATION

BACKGROUND

The present application relates generally to an improved data processing apparatus and method and more specifically to mechanisms for providing accessibility of virtual environments via echolocation.

Echolocation is a process by which sound waves are used to assist with navigation. A sound source emits a sound wave and measures the reflected sound wave that reflects off of objects to thereby identify the presence, size, shape, and relative location of objects within a physical environment. Both animals and human beings utilize echolocation to identify objects in their physical environment.

In particular echolocation allows human beings with visual impairments to stimulate the visual processing portion of the brain to allow them to build a "visual" map of their environment. It has been shown that echolocation can allow a visually impaired person to independently navigate their physical environment, including participating in tasks such as hiking and riding a bicycle.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method, in a data processing system comprising a memory configured with instructions for execution by a processor of the data processing system to configure the processor to implement an echolocation engine. The method comprises receiving, by the echolocation engine executing on the data processing system, graphical information for a virtual environment, and analyzing, by the echolocation engine, the graphical information to detect a virtual object present in the virtual environment. The method further comprises identifying, by the echolocation engine, one or more characteristics of the detected virtual object. The one or more characteristics comprise a relative location of the virtual object to a virtual representation of a user in the virtual environment. The method also comprises generating, by the echolocation engine, echo data defining characteristics of an audio output that represents the virtual object in a manner emulating an echo of a sound emitted from the virtual representation of the user in the virtual environment. The characteristics of the audio output comprise an identification of one or more audio output devices to output the audio output based on the relative location of the virtual object to the virtual representation of the user. Furthermore, the method comprises controlling, by the echolocation engine, output of the audio output by the one or more audio output devices based on the generated echo data.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE SEVERAL VIEWS OF THE DRAWINGS

The invention, as well as a preferred mode of use and further objectives and advantages thereof, will best be understood by reference to the following detailed description of illustrative embodiments when read in conjunction with the accompanying drawings, wherein.

DETAILED DESCRIPTION

Figure 1A:
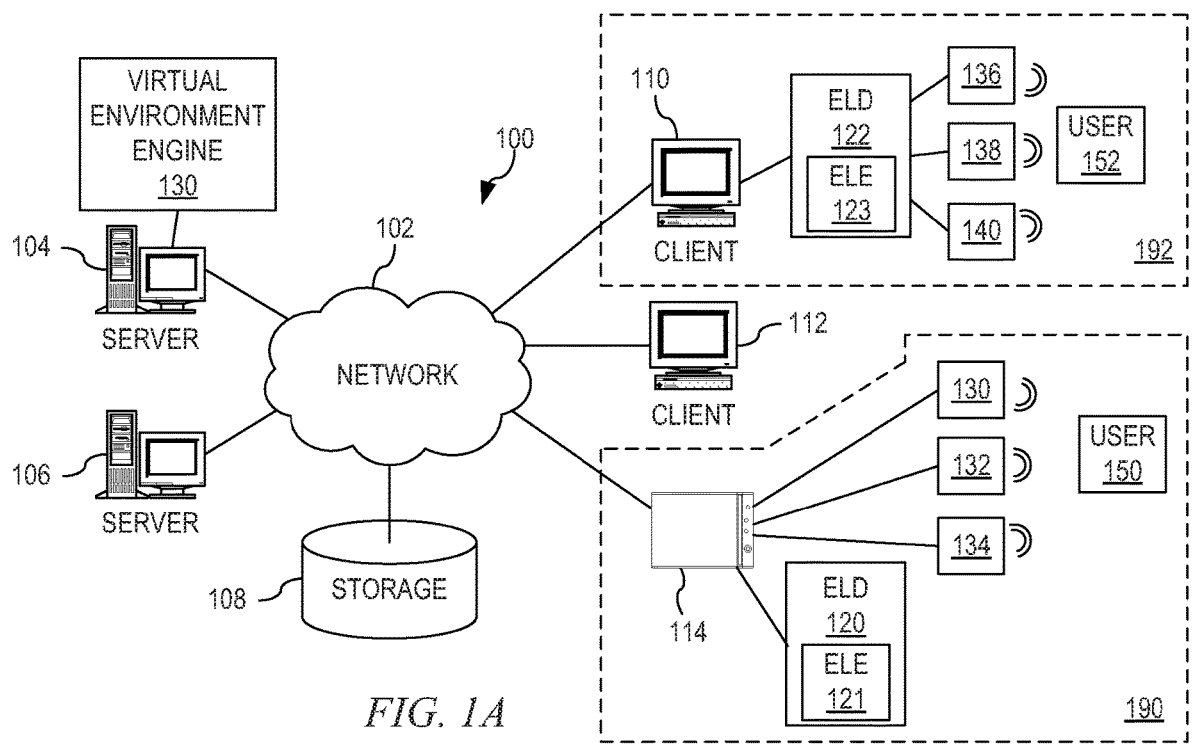
FIG. 1A depicts a pictorial representation of an example distributed data processing system in which aspects of the illustrative embodiments may be implemented for an embodiment in which the echolocation functionality is provided by a stand-alone echolocation appliance or echolocation computing device coupled to a corresponding computing device.

Virtual environments, such as those that may be found in many modern-day video games and the like, rely heavily on visual representations, hence the name "video" games. As such, it is difficult for visually impaired persons to have a similar experience of the virtual environment to persons that are not visually impaired. However, people who are visually impaired may be able to interpret many audible cues from the virtual environment, such as music or noises caused when certain areas of the virtual environment are encountered, when certain actions are performed, and the like. However, visually impaired persons cannot generally engage in the full immersive experience of the virtual environment because these audible cues are not sufficient to give them a strong understanding of the virtual environment and the virtual objects present within that virtual environment.

The illustrative embodiments provide mechanisms for adapting echolocation to virtual environments to allow visually impaired persons to be able to interact with the virtual environment. The virtual environment is a virtual representation of a physical environment, whether actually present in the real world or a fantastical environment, generated by a computing device executing corresponding software having instructions for generating the virtual environment. A user, or a virtual avatar or character representing the user, may be represented in the virtual environment, or the view of the virtual environment presented to the user may be from the perspective of the virtual avatar or character as if the user were looking through the eyes of the virtual avatar or character. The virtual environment typically has virtual objects or elements (generally referred to herein as "objects") with which the user, either directly or via a virtual avatar or character, interacts. In the context of a video game, the virtual environment may be a portion of a virtual world generated by software executing on one or more computing devices, e.g., server computing devices, client computing devices, or the like. A user of a client computing device may interact with the virtual world or virtual environment via user inputs made by the user via their client computing device and one or more peripheral devices associated with the client computing device. Examples of virtual environments and virtual worlds include many currently known massively multiplayer online (MMO) computer games, first person video games, and the like.

While the following description will assume that the virtual environment is part of a video game in which the game player, i.e. the user, interacts with a virtual environment of the video game, it should be appreciated that the illustrative embodiments are not limited to such. Rather, the mechanisms of the illustrative embodiments may be implemented with any virtual environment, whether a video game or otherwise, in which a user provides input to interact with objects within a virtual environment and receives output feedback indicative of the results of the user's interaction with the virtual environment. For example, some implementations may be with regard to virtual environments for virtual conferencing, virtual environment based social networking computing systems, or the like.

The concept of echolocation relies on short tones that change audibly based on distance and the composition of the objects which reflect the tones (louder=closer, quieter=further away, delay=density, etc.). Echolocation is based on the concept that an emitted tone would bounce off an object and return to the origin in a constant amount of time given a constant distance. If the object is nearer, the distance is less and the sound is louder. Mimicking this "bounce off" behavior is key to this being feasible to a visually impaired person who has learned to employ echolocation in navigating the real world. The illustrative embodiments allow a human user to apply what they are able to do with real objects to virtual objects present in a virtual environment.

In adapting echolocation to virtual environments, the illustrative embodiments provide mechanisms for analyzing the position of a virtual representation of the user (referred to hereafter as a "virtual player") relative to objects in the virtual environment in either a two-dimensional or three-dimensional environment. This mechanism may be implemented as a stand-alone device or appliance that may be coupled to a computing device, video game console, or the like, such that modifications to the software generating the virtual environment is not necessary. The mechanisms of the illustrative embodiments, e.g., the stand-alone echolocation device, may translate distance information for the virtual player relative to elements of the virtual environment into echolocation "pings" that may be emitted from one or more connected audio output devices, e.g., speakers.

In some illustrative embodiments, the echoes, or "pings", are sounds generated by the mechanisms of the illustrative embodiments that emulate an echo of a sound emitted from a virtual representation of the user in the virtual environment. For example, the echo or ping emulates the virtual avatar or virtual player of the user emitting a sound and that same sound being reflected back to the user from objects within the virtual environment such that the user is informed of the relative location, position, and distance of the objects. In such embodiments, the echoes or "pings" may have characteristics that are not modified from the virtual sound emitted by the virtual player other than to possibly modify the pitch/volume of the sound based on the target object's distance, materials, etc. In this way, the echoed sound is kept relatively constant in nature with the only differences in pitch/volume being based on a small set of characteristics of the target object. In this way, the mechanisms of the illustrative embodiments mimic or recreate the experience that a real person would have in the virtual environment if they employed echolocation to bounce a sound off a target object to thereby identify its location, position, and distance, and track the objects movement, if any.

In some illustrative embodiments, the characteristics of the pings may be changed more significantly to represent different characteristics of the virtual objects within the virtual environment that are represented by the pings. For example, in a video game implementation, the pitch, frequency, tone, or any other audible characteristic of the pings may be modified based on the characteristics of the virtual objects, e.g., different tones for objects representing friendly characters, different tones for enemy characters, different pitch or frequency for objects at different distances or elevations from the virtual avatar or character, etc. However, even in these illustrative embodiments, the complexity of the tones is maintained as small as possible so as to enable human users to utilize their capabilities for echolocation in the real world to be applied to the tones that they hear representing the virtual objects in the virtual environment.

The echolocation device preferably obtains graphical information about the virtual environment from an associated computing device used to render the virtual environment, e.g., the users client computing device or the like. The graphical information may be obtained through a screen scraping technique that captures images of a screen, from the graphical application programming interfaces (APIs), e.g., DirectX, OpenGL, or the like, by capturing a digital feed of what is being rendered, or any other suitable method for capturing graphical information describing what is being rendered by the graphics processor, graphics adapter, or other graphic output device of the computing device. In the case of an implementation obtaining the graphical information from the APIs, the captured graphical information may provide a higher-fidelity and lower latency image stream than the screen scraping technique.

Having obtained the graphical information from the graphics information source, whether the APIs, through screen scraping, or the like, the graphical information is then analyzed to identify objects present in the virtual environment relative to the virtual avatar or character representing the user. In order to perform such analysis, edge detection mechanisms may be utilized. Edge detection is an image processing technique for finding the boundaries of objects within images. Edge detection operates by detecting sharp differences in brightness to perform image segmentation which identifies the outlines of objects present within a video image.

The outlines of the objects in the virtual environment may be used to identify relative positions of objects to the virtual avatar or character (referred to hereafter simply as the "avatar"). Moreover, the outlines of the objects may be matched against a database of objects so as to match the outline characteristics to characteristics of objects in the database and thus, identify the object. The characteristics of the object may be utilized to specify a type of the object, a size of the object, whether the object is a friend or a foe, and the like. The size of the object may be utilized along with the graphical information obtained to determine a relative distance from the virtual avatar or character representing the user, e.g., knowing the size of the virtual avatar or character, and the size of the object, and the size of the representation of the object in the video image, the distance of the object from the virtual avatar or character may be calculated and used to control characteristics of the pings generated in association with the object.

It should be appreciated that other object detection techniques may also be utilized, depending on the desired implementation. For example, object detection may be performed using deep learning techniques that can be trained to recognize objects and what the object is. These techniques can be trained globally or for an individual data set (game/application) to improve accuracy. Moreover, the objects detected in one frame of a video stream may be tracked over multiple frames and the relative size of the object, as well as any obscuring of an object by other objects, may be used to help determine whether the object is coming towards/away from the user.

Based on the identification of objects in the virtual environment, their relative directions and distances from the avatar, and other characteristics of the objects obtained, for example, from the matching of the object to objects in the object database, audible outputs may be generated from one or more audio output devices, e.g., speakers, that are specific to the particular objects. These audible outputs, which for illustrative purposes only will be assumed to be "pings", may be output from speakers so as to represent the direction of the object relative to the avatar. As noted above, in some illustrative embodiments, the pings represent an echo of an emitted sound from the avatar as if the avatar were using echolocation in the virtual environment, such that any differences from the emitted sound and the echo would be based on the distance to the object from which the echo was reflected, and any material characteristics of that object, e.g., density of the object.

In some illustrative embodiments, the echoed sounds may have other modifications to their characteristics that represent the characteristics of the object within the virtual environment, e.g., friend/foe status of the virtual object relative to the user, etc. For example, if the object is a foe, then the ping may have a different tone than objects that are friendly or neutral to the user. If the object is relatively far away, as may be determined from a comparison of the determined distance of the object relative to the avatar to one or more pre-defined threshold values (e.g., close, middle, and far distance thresholds), then the audible output may have a lower pitch than that of an object that is relatively closer to the avatar. Various characteristics of the identified objects in the virtual environment may be conveyed in the characteristics of the audio output generated by the audio output devices. It should be appreciated, however, that the basic characteristics of the echoes emulate real-world echo-location and thus, represent an original sound that may be emitted by from the virtual avatar of the user in the virtual environment, with characteristics of the echo representing echoes from virtual objects as if they were physical objects within a physical environment reflecting the original sound. The echo of the echolocation emulates actual physics of a physical environment but with regard to virtual objects in a virtual environment. The additional modifications of the characteristics of the echoed sounds may be made to these basic sounds so as to reflect the additional characteristics of the object as noted above.

The particular audio output devices, e.g., speakers, that output the audio output may be controlled based on the relative position and distance from the avatar. For example, in a two-dimensional virtual environment, a two speakers physically present to the left and right of the user may be utilized to output the audio output. However, in a three-dimensional virtual environment, a plurality of speakers, e.g., three or more, may be utilized in a surround sound manner so as to represent different objects in different directions relative to the user. For example, if the object is determined to be to the right of the avatar, a speaker physically present to the right of the user will be utilized to output the audio output representing the identified object. Thus, the echolocation device of the illustrative embodiments will drive the audio output to the attached audio output devices so as to represent the relative position of the object to the avatar by outputting the audio output via an audio output device relatively positioned to the user that is positioned in a similar manner of the object to the avatar.

It should be appreciated that the illustrative embodiments may operate continuously, periodically, or in response to the occurrence of particular events which initiate the operation of the echolocation device on newly captured images of the virtual environment. For example, the echolocation device may receive, on a continuous basis, a stream of graphical information from the graphics APIs of the associated computing device which may be used to continuously generate audio outputs representing the identified objects in the virtual environment. As such, the echolocation device may discern movements of objects within the virtual environment and may further represent the movement in characteristics of the audio output. For example, more frequent audio outputs may be generated as the object moves closer to the avatar, and less frequent audio outputs may be generated as the object moves away from the avatar. Alternatively, the pitch of the audio output for the object may be increased as the object moves closer to the avatar, and reduced as the object moves further away from the avatar, similar to a Doppler Effect. Such movement may also be identified through periodic operations of the echolocation device as well.

With regard to the occurrence of particular events that trigger the operation of the echolocation device, examples of such events may be a change in the user's avatar position within the virtual environment, the input of a request by the user to perform the echolocation operation of the echolocation device, or the like. In some illustrative embodiments, the event may be an audio input from the user, such that the user may initiate their own vocal ping which may be used to generate an echo effect, e.g., a replay of the audio input as an output with modifications made to represent the locations, distances, and characteristics of the objects identified as being present within the virtual environment.

It should also be appreciated that, in some illustrative embodiments, the operations of the echolocation device may be applied to only a subset of actual objects within the virtual environment. That is, in virtual environments there may be hundreds or even thousands of virtual objects represented in the virtual environment. Not all of these virtual objects can be feasibly represented as echoes, i.e. audio outputs representing objects in the virtual environment. The illustrative embodiments may limit the operation of the echolocation device to only those objects that are relatively more important, as determined from a pre-defined configuration of the echolocation device. For example, when embedded into a graphical modeling system (OpenGL, DirectX, or the like) the model may indicate which objects can be interacted with by the user and which object are background objects. In a screen scrape approach, the illustrative embodiments may track all geometries that are moving "together" and track them as one entity. Thus, for example, if a virtual apple is sitting on a virtual table in the virtual environment, it may be treated as a background and only "boundary" pings would return any information. However, if the same apple is moving in the virtual space, e.g., thrown at the virtual avatar or falling from a tree, it may warrant its own ping indicating movement or activity that a visually-capable person would also normally pick up on. Other mechanisms for discerning between relatively important objects that should provide echoes, and those that do not provide such echoes, or provide less complex echoes, may be used without departing from the spirit and scope of the illustrative embodiments.

It should be appreciated that while the illustrative embodiments may be implemented as a stand-alone device, referred to above as the echolocation device, the illustrative embodiments are not limited to such. Rather, in some illustrative embodiments, the mechanisms and functionality of the echolocation device may be integrated into and operate as part of the computing device, video game console, or other virtual environment rendering device. The echolocation device functionality may be provided as an accessibility feature of the virtual environment software and/or device itself. Moreover, three-dimensional geometry may be used to accurately and efficiently identify objects that are the basis for the generation of echoes in accordance with the illustrative embodiments.

Thus, the illustrative embodiments provide mechanisms for presenting echolocation outputs to assist visually impaired persons in discerning the presence, relative location, and other characteristics of objects within a virtual environment. The mechanisms of the illustrative embodiments may be implemented in a stand-alone device or integrated into computer and software used to generate virtual environments. The echolocation functionality of the illustrative embodiments improves the way in which the computing elements represent the virtual environment to visually impaired persons such that interactions between visually impaired persons and objects present in the virtual environment is made more user friendly and more accessible.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general-purpose hardware, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine-readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As noted above, the present invention provides mechanisms for providing an echolocation output representing virtual objects (or simply "objects") in a virtual environment in order to make the virtual environment more accessible to visually impaired persons. The echolocation output provides indications as to the relative location and distance of the virtual objects to a viewpoint of the user, e.g., a virtual avatar or character representing the user in the virtual environment. Moreover, characteristics of the virtual object may be conveyed in the particular echolocation outputs (also referred to as echoes) generated by the echolocation device of the illustrative embodiments. Thus, a visually impaired person is given a greater understanding of the objects present in the virtual environment with which the user is interacting via their avatar or character.

Figure 1B:
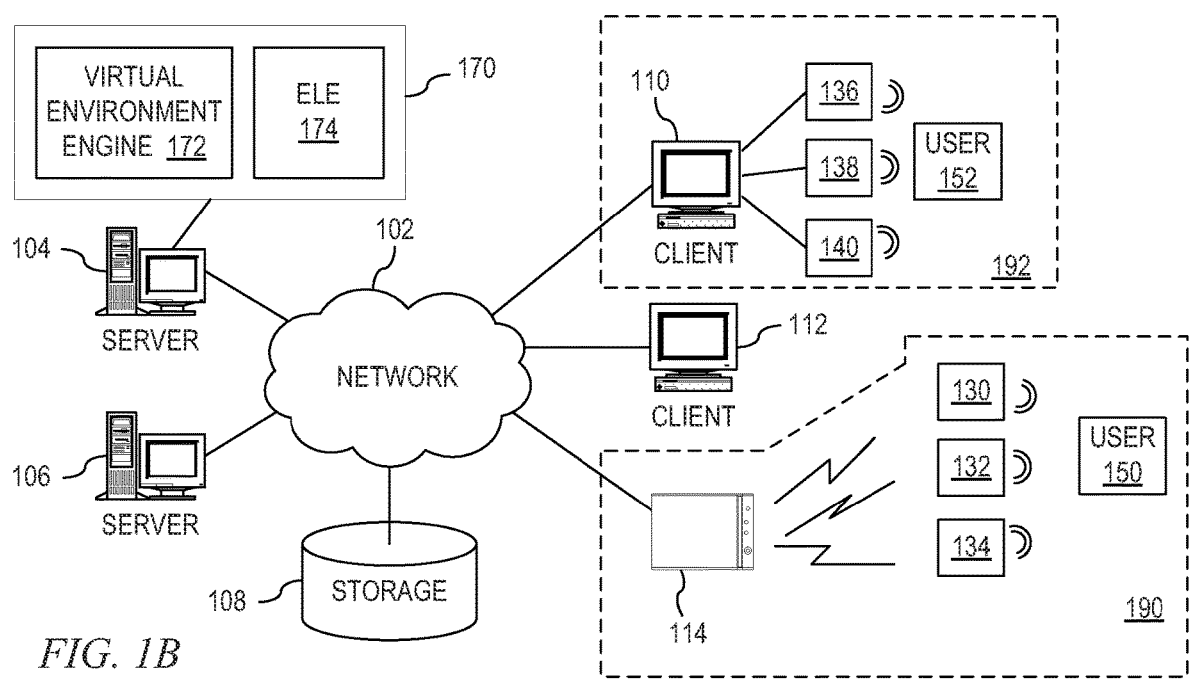
FIG. 1B depicts a pictorial representation of an example distributed data processing system in which aspects of the illustrative embodiments may be implemented for an embodiment in which the echolocation functionality is provided by the same server, or server farm/cluster, that provides the virtual environment rendering information to client computing devices.
Figure 2:
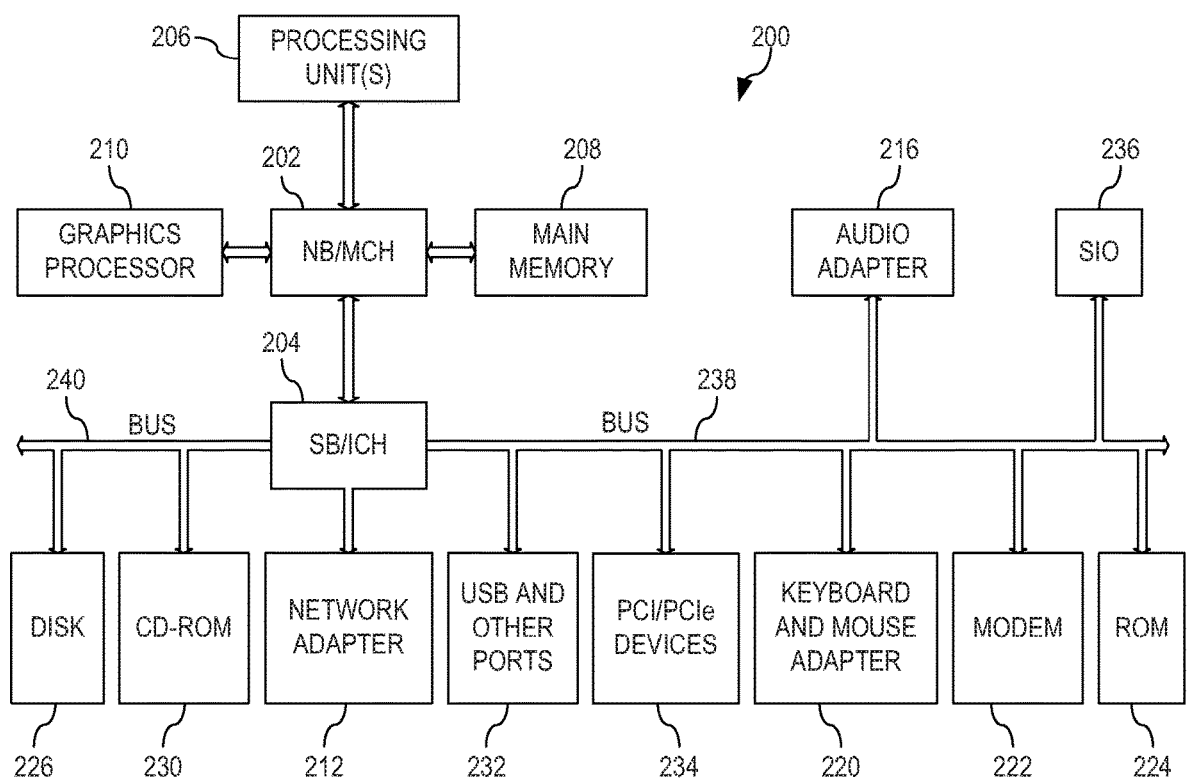
FIG. 2 is a block diagram of just one example data processing system in which aspects of the illustrative embodiments may be implemented.

The illustrative embodiments may be utilized in many different types of data processing environments. In order to provide a context for the description of the specific elements and functionality of the illustrative embodiments, FIGS. 1A, 1B, and 2 are provided hereafter as example environments in which aspects of the illustrative embodiments may be implemented. It should be appreciated that FIGS. 1A, 1B, and 2 are only examples and are not intended to assert or imply any limitation with regard to the environments in which aspects or embodiments of the present invention may be implemented. Many modifications to the depicted environments may be made without departing from the spirit and scope of the present invention.

FIGS. 1A and 1B depict alternative embodiments for implementing an echolocation functionality for virtual environments. FIG. 1A depicts a pictorial representation of an example distributed data processing system in which aspects of the illustrative embodiments may be implemented for an embodiment in which the echolocation functionality is provided by a stand-alone echolocation appliance or echolocation computing device coupled to a corresponding computing device, e.g., a server or client computing device. FIG. 1B depicts a pictorial representation of an example distributed data processing system in which aspects of the illustrative embodiments may be implemented for an embodiment in which the echolocation functionality is provided by the same server, or server farm/cluster, that provides the virtual environment rendering information to client computing devices.

With reference to FIG. 1A, distributed data processing system 100 may include a network of computers in which aspects of the illustrative embodiments may be implemented. The distributed data processing system 100 contains at least one network 102, which is the medium used to provide communication links between various devices and computers connected together within distributed data processing system 100. The network 102 may include connections, such as wire, wireless communication links, or fiber optic cables.

In the depicted example, server 104 and server 106 are connected to network 102 along with storage unit 108. In addition, clients 110, 112, and 114 are also connected to network 102. These clients 110, 112, and 114 may be, for example, personal computers, network computers, or the like. In the depicted example, server 104 provides data, such as boot files, operating system images, and applications to the clients 110, 112, and 114. Clients 110, 112, and 114 are clients to server 104 in the depicted example. Distributed data processing system 100 may include additional servers, clients, and other devices not shown.

In the depicted example, distributed data processing system 100 is the Internet with network 102 representing a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, consisting of thousands of commercial, governmental, educational and other computer systems that route data and messages. Of course, the distributed data processing system 100 may also be implemented to include a number of different types of networks, such as for example, an intranet, a local area network (LAN), a wide area network (WAN), or the like. As stated above, FIG. 1 is intended as an example, not as an architectural limitation for different embodiments of the present invention, and therefore, the particular elements shown in FIG. 1 should not be considered limiting with regard to the environments in which the illustrative embodiments of the present invention may be implemented.

As shown in FIG. 1A, a separate and specifically configured computing device may be provided that is a stand-alone echolocation device 120, 122 for providing echolocation functionality with regard to virtual environments generated by another computing device, e.g., server 104. Alternatively, as will be described in greater detail hereafter with regard to FIG. 1B, one or more of the computing devices, e.g., server 104, may be specifically configured to implement a virtual environment generation engine 172 with echolocation functionality provided by an echolocation engine 174.

In either embodiment, the configuring of the computing device, e.g., server 104 and/or separate stand-alone echolocation device 120, 122 to provide echolocation functionality in accordance with the illustrative embodiments, may comprise the providing of application specific hardware, firmware, or the like to facilitate the performance of the operations and generation of the outputs described herein with regard to the illustrative embodiments. The configuring of the computing device, e.g., server 104 and/or separate stand-alone echolocation device 120, 122 may also, or alternatively, comprise the providing of software applications stored in one or more storage devices and loaded into memory of a computing device, such as server 104, for causing one or more hardware processors of the computing device to execute the software applications that configure the processors to perform the operations and generate the outputs described herein with regard to the illustrative embodiments. Moreover, any combination of application specific hardware, firmware, software applications executed on hardware, or the like, may be used without departing from the spirit and scope of the illustrative embodiments.

It should be appreciated that once the computing device, e.g., server 104 or stand-alone device 120, 122 is configured in one of these ways, the computing device becomes a specialized computing device specifically configured to implement the mechanisms of the illustrative embodiments and is not a general-purpose computing device. Moreover, as described hereafter, the implementation of the mechanisms of the illustrative embodiments improves the functionality of the computing device and provides a useful and concrete result that facilitates the generation and outputting of audible signals, via audio output devices, such as speakers, that present echoes of an echolocation functionality that indicates characteristics of, and the relative location of, virtual objects within a virtual environment. For example, these echoes may be "ping" outputs that indicate to a visually impaired person information about virtual objects present in a virtual environment that the visually impaired person interacts with via an avatar or character. The echoes may specify the relative location of the virtual objects relative to the avatar or character via a similar directional mapping of the virtual object relative to the avatar or character, and the relative position of speakers to the user in the physical environment in which the user is present.

As shown in FIG. 1A, with a stand-alone device embodiment, the echolocation computing device (ELD) 120, 122, may be associated with a host computing device, gaming console device, or other source 110, 114 of video/audio output for rendering a virtual environment with which a user 150, 152 interacts through inputs provided via a peripheral device (not shown) associated with the host system 110, 114. In addition, the ELD 120, 122, may be coupled to corresponding audio output devices, e.g., speakers 130-140, through which audio outputs are provided that are audio outputs corresponding to the rendering of the virtual environment, as well as echolocation audio outputs, such as "pings" or other audio outputs used for echolocation purposes, referred to collectively as "echoes" herein. The speakers 130-132 may be coupled directly to the ELD 120, 122 via wired or wireless connections or may be coupled to the host system 110, 114 with which the ELD 120, 122 provides command and/or data input to cause the host system 110, 114 to output the echoes.

In accordance with one illustrative embodiment, a server 104 may execute software that generates a virtual environment, e.g., a virtual environment generation engine 160, and provides data to client devices, such as host systems 110, 114, to cause them to render the virtual environment locally on the host systems 110, 114. Moreover, the software executing on the server 104 may receive inputs from the users 150, 152 representing the user's commands for controlling their virtual avatar or character within the virtual environment. These inputs may be processed by the software executing on the server 104 to update the virtual environment via the virtual environment generation engine 160 and provide updated data to the client devices 110, 114 to update the rendering of the virtual environment on the client devices 110, 114. For example, the software executing on the server 104 may be a video game software, such as a massively multiplayer online (MMO) video game, a virtual conferencing software, a virtual environment social networking software, or the like.

In response to receiving data from the server 104 for rendering the virtual environment at the client computing device 110, 114, the client computing device (host device) 110, 114, processes the data to generate video and audio output data that is rendered using corresponding video output devices (not shown) and audio output devices 130-140. The ELD devices 120-122, executing echolocation engines (ELEs) 121, 123, capture data representing the video output of the virtual environment rendered by the client computing device (host device) 110, 114, i.e. captured virtual environment data. The captured virtual environment data may be analyzed by the ELEs 121, 123 to determine the position of a virtual representation of the user (referred to hereafter as a "virtual player") relative to objects in the virtual environment in either a two-dimensional or three-dimensional environment. As mentioned previously, various technologies may be utilized to obtain this captured virtual environment data, including, but not limited to, screen scraping technology, interfacing with graphics APIs (e.g., DirectX, OpenGL, etc.) of the client computing devices 110, 114 from which graphical data may be obtained, edge detection technology, and the like.

The ELEs 121, 123 translate distance information for the virtual player relative to objects of the virtual environment into echoes, e.g., echolocation "pings," that may be emitted from the corresponding speakers 130-140. Characteristics, e.g., pitch, frequency, tone, duration, patterns of outputs, etc., of the echoes may be selected and used to generate different echo outputs representing different characteristics of the objects within the virtual environment rendered by the client computing systems 110, 114. As mentioned above, an example of such different characteristics may include, for a video game implementation, different tones for objects representing friendly characters, different tones for enemy characters, different pitch or frequency for objects at different distances from the virtual avatar or character (virtual player), etc. may be used to provide a virtual audio environment (VAE) for visually impaired persons.

Thus, through analysis of the captured virtual environment data, such as by using edge detection technology or the like, the outlines of the objects in the virtual environment may be used to identify relative positions and distances of objects to the virtual avatar or character (virtual player) within the virtual environment. The relative positions and distances may involve computations based on the relative sizes of the objects and the virtual avatar or character, as may be determined from a matching of the outlines of the objects with a database of known objects for the particular virtual environment. For example, databases of virtual objects may be provided for the particular virtual environments that are generated by the software executing on the server 104, e.g., particular virtual objects for the video game software.

The outlines of the objects may be matched against entries in the database of objects so as to match the outline characteristics to characteristics of objects in the database and thus, identify the object. The entries in the database may comprise the characteristics of the object which may be utilized to specify a type of the object, a size of the object, whether the object is a friend or a foe, and the like. The size of the object may be utilized along with the graphical information obtained to determine a relative distance from the virtual avatar or character representing the user, e.g., knowing the size of the virtual avatar or character, and the size of the object, and the size of the representation of the object in the video image, the distance of the object from the virtual avatar or character may be calculated and used to control characteristics of the echoes generated in association with the object.

Based on the identification of objects in the virtual environment, their relative directions and distances from the avatar, and other characteristics of the objects obtained, for example, from the matching of the object to objects in the object database, echo outputs may be generated by the ELEs 121, 123 of the ELDs 120, 122 and output to the user 150, 152 in their physical environment 190, 192 from the corresponding speakers 130-140, where each echo may be specific to the particular objects in the virtual environment. The echoes are output from respective ones of the speakers 130-140 in the particular physical environments 190, 192 so as to represent the direction of the object relative to the avatar, the distance of the object from the avatar, and characteristics of the object, e.g., friend, foe, relative size, whether the object is approaching or retreating, etc. For example, if the object is to the right side of the virtual avatar in the virtual environment, a speaker 136 that is relatively positioned to the right of the user 152 in the physical environment 192 may be used to output the echo corresponding to that object. Moreover, if the object is a foe, then the echo may have a different tone than objects that are friendly or neutral to the user's avatar or character in the virtual environment. If the object is relatively far away, as may be determined from a comparison of the determined distance of the object relative to the avatar to one or more pre-defined threshold values (e.g., close, middle, and far distance thresholds), then the echo, which at a basic level mimics a change in volume, pitch, etc. of a sound that bounces off of an object in a physical environment, may also have its characteristics modified, in some illustrative embodiments, to reflect other characteristics of the virtual object, e.g., have a lower pitch, volume, or the like, than that of an object that is relatively closer to the avatar. Various characteristics of the identified objects in the virtual environment may be conveyed in the characteristics of the echoes generated by the ELEs 121, 123 of the ELDs 120, 122 and output via the speakers 130-140.

It should be appreciated that the characteristics of the echoes may be further modified to reflect the material of the virtual object from which the sound was virtually reflected, e.g., an increased delay for more dense objects, different pitches for different materials, and the like. For example, if the virtual object is a "foe" object that is a wolf, the echoed sound may soften more than if the virtual object were a knight in armor. Such modifications of the echoed sounds may provide a further cue to the user to differentiate types of virtual objects from which echoes are obtained.

As noted previously, the particular speakers 130-140 that output the audio output may be controlled based on the relative position and distance from the avatar. For example, in a two-dimensional virtual environment, a single speaker physically present directly in front of the user may be utilized to output the audio output. However, in a three-dimensional virtual environment, a plurality of speakers 130-134 for physical environment 190 and speakers 136-140 for physical environment 192, may be utilized in a surround sound manner so as to represent different objects in different directions relative to the user. Thus, the echolocation devices 120, 122 of the illustrative embodiments will drive the audio output to the coupled speakers 130-140 so as to represent the relative position of the object to the avatar by outputting the echo via a speaker 130-140 relatively positioned to the user that is positioned in a similar manner of the object to the avatar.

The echolocation devices (ELDs) 120, 122 may operate continuously, periodically, or in response to the occurrence of particular events which initiate the operation of the ELD 120, 122 on newly captured images of the virtual environment. For example, the ELD 120, 122 may receive, on a continuous basis or a periodic basis, graphical data from the graphics APIs of the associated client computing device 110, 114, such as via a data stream, or from screen scraping, which may be used to continuously generate echoes representing the identified objects in the virtual environment. In such a case, the ELDs 120, 122 may discern movements of objects within the virtual environment and may further represent the movement in characteristics of the echoes. For example, more frequent echoes may be generated as the object moves closer to the avatar, and less frequent echoes may be generated as the object moves away from the avatar. Alternatively, the pitch of the echoes for the object may be increased as the object moves closer to the avatar, and reduced as the object moves further away from the avatar, similar to a Doppler effect.

The operation of the echolocation devices 120, 122 may be triggered in response to particular events, such as a change in the user's avatar position within the virtual environment, the input of a request by the user to perform the echolocation operation of the echolocation device, the user audibly providing a trigger sound via an audio input device, e.g., the user initiating an echo triggering sound, or the like. Any type of triggering event may be used, depending on the particular implementation, which is suitable to the particular application of the echolocation functionality.

As noted above, the operations of the ELDs 120, 122 may be applied to only a subset of actual objects within the virtual environment since such virtual environments may comprise large numbers of virtual objects. In order to not overwhelm the user 150, 152 with the number of echoes being output via the speakers 130-140, the ELDs 120-122 may limit their operation to only those objects that are relatively more important, as determined from a pre-defined configuration of the ELDs 120-122.

It should be appreciated that while the illustrative embodiments may be implemented as a stand-alone device 120, 122, in some illustrative embodiments, the mechanisms and functionality of the ELDs 120, 122 may be integrated into and operate as part of the computing device, video game console, or other virtual environment rendering device 110, 114. The ELD 120, 122 functionality may be provided as an accessibility feature of the virtual environment software and/or device itself. Moreover, three-dimensional geometry may be used to accurately and efficiently identify objects that are the basis for the generation of echoes in accordance with the illustrative embodiments.

Moreover, as shown in FIG. 1B, rather than integrating the ELD 120, 122, and ELE 121, 123 functionality into the client computing devices 110, 114 themselves, the functionality of these elements 120-123 may be integrated in the software executing on the server 104 such that the server 104 may not only provide the virtual environment data for rendering the virtual environment on the client devices 110, 114, but may also provide data representing the echoes to be output by the client computing devices 110, 114 via their associated speakers 130-140. As shown in FIG. 1B, the server 104 may further execute, in addition to the virtual environment generation engine 172, echolocation engine 174 which may obtain the virtual environment information directly from the virtual environment generation engine 172 and may generate echoes, such as in the manner previously described, with the resulting echo data being provided to the client computing devices 110, 114, via the network 102 along with the virtual environment data from the virtual environment generation engine 172. Thus, a separate device 120, 122 is not required to be coupled to the client computing devices 110, 114 and the client computing devices 110, 114 do not need to be modified in any manner.

Thus, the illustrative embodiments provide mechanisms for presenting echolocation outputs, i.e. echoes, to assist visually impaired persons in discerning the presence, relative location, and other characteristics of objects within a virtual environment. The mechanisms of the illustrative embodiments may be implemented in a stand-alone device or integrated into computer and software used to generate virtual environments, either in a client computing device location or a server computing device location. The echolocation functionality of the illustrative embodiments improves the way in which the computing elements represent the virtual environment to visually impaired persons such that interactions between visually impaired persons and objects present in the virtual environment is made more user friendly and more accessible.

As noted above, the mechanisms of the illustrative embodiments utilize specifically configured computing devices, or data processing systems, to perform the operations for providing echolocation functionality to assist visually impaired persons in discerning the presence of objects in a virtual environment. These computing devices, or data processing systems, may comprise various hardware elements which are specifically configured, either through hardware configuration, software configuration, or a combination of hardware and software configuration, to implement one or more of the systems/subsystems described herein. FIG. 2 is a block diagram of just one example data processing system in which aspects of the illustrative embodiments may be implemented. Data processing system 200 is an example of a computer, such as server 104 in FIG. 1, in which computer usable code or instructions implementing the processes and aspects of the illustrative embodiments of the present invention may be located and/or executed so as to achieve the operation, output, and external effects of the illustrative embodiments as described herein. Data processing system 200 may also be configured as a client computing device, such as client 110-114 in FIG. 1.

Moreover, in accordance with one or more of the illustrative embodiments set forth herein, the data processing system 200 may be specifically configured with appropriate hardware, software executing on hardware, firmware, or the like, to implement the echolocation functionality of the illustrative embodiments in a separate stand-alone device. In such an embodiment, elements of the depicted data processing system that are determined to not be integral to the performance of the echolocation functionality may be eliminated from the configuration of the data processing system 200. For example, if the stand-alone device itself is not going to be outputting video or audio outputs itself, then such interfaces may be eliminated, if the stand-alone device is not going to be reading/writing data or executing instructions read from a CD-ROM, then the CD-ROM drive may be eliminated from the configuration, etc. Thus, many modifications may be made to the example depicted data processing system 200 depending on the desired implementation.

In the depicted example, data processing system 200 employs a hub architecture including north bridge and memory controller hub (NB/MCH) 202 and south bridge and input/output (I/O) controller hub (SB/ICH) 204. Processing unit 206, main memory 208, and graphics processor 210 are connected to NB/MCH 202. Graphics processor 210 may be connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE) or serial advanced technology attachment (SATA) interface. Super I/O (SIO) device 236 may be connected to SB/ICH 204.

An operating system runs on processing unit 206. The operating system coordinates and provides control of various components within the data processing system 200 in FIG. 2. As a client, the operating system may be a commercially available operating system such as Microsoft® Windows 10®. An object-oriented programming system, such as the Java™ programming system, may run in conjunction with the operating system and provides calls to the operating system from Java™ programs or applications executing on data processing system 200.

As a server, data processing system 200 may be, for example, an IBM eServer™ System P® computer system, Power™ processor-based computer system, or the like, running the Advanced Interactive Executive (AIX®) operating system or the LINUX® operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and may be loaded into main memory 208 for execution by processing unit 206. The processes for illustrative embodiments of the present invention may be performed by processing unit 206 using computer usable program code, which may be located in a memory such as, for example, main memory 208, ROM 224, or in one or more peripheral devices 226 and 230, for example.

A bus system, such as bus 238 or bus 240 as shown in FIG. 2, may be comprised of one or more buses. Of course, the bus system may be implemented using any type of communication fabric or architecture that provides for a transfer of data between different components or devices attached to the fabric or architecture. A communication unit, such as modem 222 or network adapter 212 of FIG. 2, may include one or more devices used to transmit and receive data. A memory may be, for example, main memory 208, ROM 224, or a cache such as found in NB/MCH 202 in FIG. 2.

As mentioned above, in some illustrative embodiments the mechanisms of the illustrative embodiments may be implemented as application specific hardware, firmware, or the like, application software stored in a storage device, such as HDD 226 and loaded into memory, such as main memory 208, for executed by one or more hardware processors, such as processing unit 206, or the like. As such, the computing device shown in FIG. 2 becomes specifically configured to implement the mechanisms of the illustrative embodiments and specifically configured to perform the operations and generate the outputs described herein with regard to the echolocation device and echolocation engine.

Those of ordinary skill in the art will appreciate that the hardware in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

Figure 3:
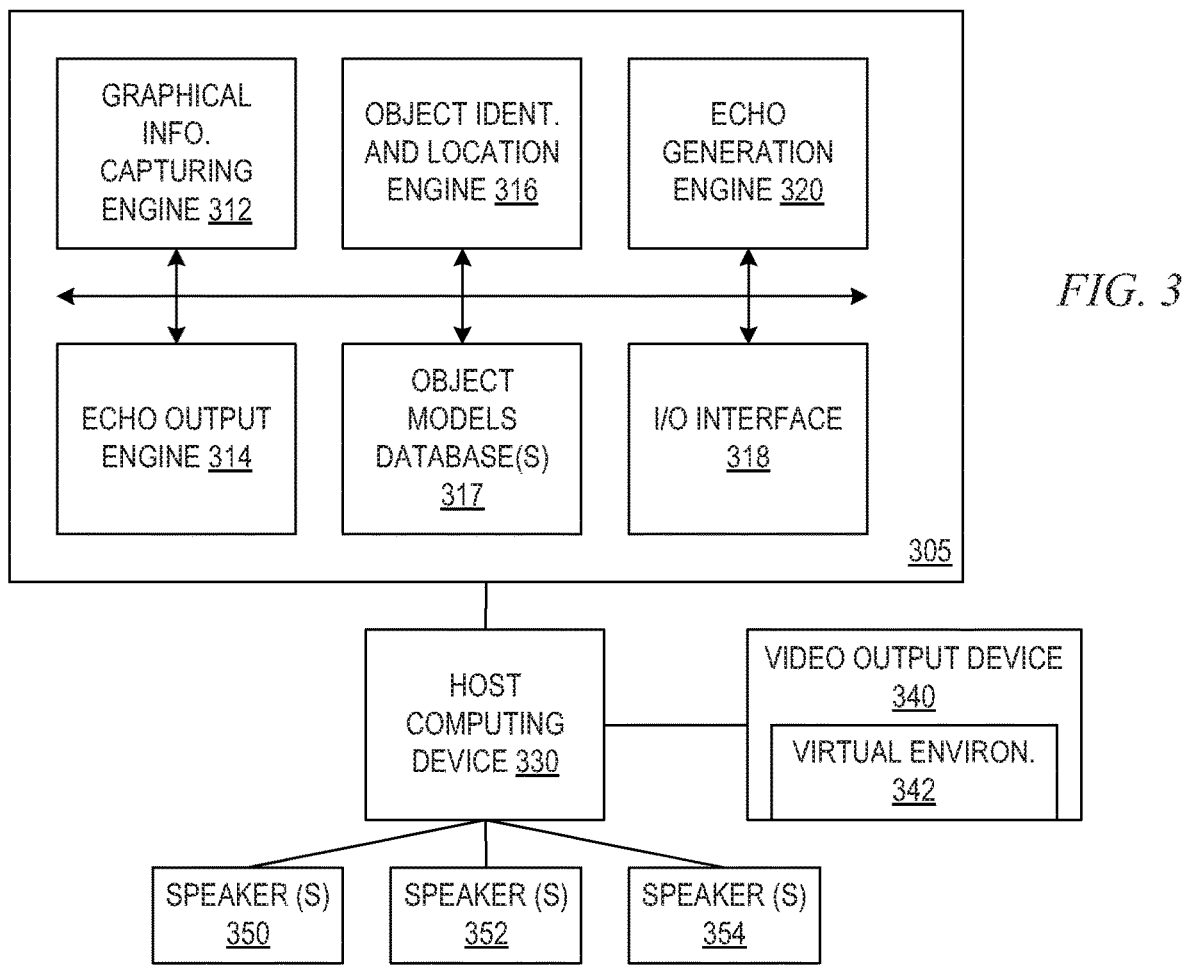
FIG. 3 is an example block diagram of the primary operational elements of an echolocation engine of an echolocation device in accordance with one illustrative embodiment.

FIG. 3 is an example block diagram of the primary operational elements of an echolocation engine of an echolocation device in accordance with one illustrative embodiment. As shown in FIG. 3, the echolocation engine (ELE) 310 includes a graphical information capturing engine 312, an echo output engine 314, an object identification and location engine 316 operating with object model database 317, input/output interface 318, and an echo generation engine 320. The ELE 310 may execute in an echolocation device (ELD) 305 which may operate in conjunction with a host computing device 330. Although the example embodiment assumes that the ELD 305 is a separate stand-alone device from the host computing device 330, it should be appreciated, as noted above, that the ELD 305 may be integrated in the host computing device 330 and/or may be integrated in a server computing device (not shown) that provides echo data remotely to the host computing device 330 via one or more data networks.

The graphical information capturing engine 312 provides logic that executes and operates to receive graphical data for a virtual environment via the input/output interface 318 and process the graphical data to identify objects present in the graphical data and an avatar or character representing the user present in the graphical data. As noted above, this processing may involve performing screen scraping, interfacing with APIs of graphics adapters or other graphics rendering devices, performing edge detection, and/or the like. As such, the graphical information capturing engine 312 generates outlines of objects present in the captured graphical data of the virtual environment, i.e. the captured virtual environment data, and provides those outlines to the object identification and location engine 316. In addition, the graphical information capturing engine 312 performs a raw determination of the relative positions of the outlines of the objects to the identified avatar or character of the user.

The object identification and location engine 316 provides logic that executes and operates to match the outlines of objects generated by the graphical information capturing engine 312 to pre-defined objects in the object models database 317. The object models database 317 stores models of each of the objects that may be represented in the virtual environment from which the graphical data is received. There may be multiple object models databases 317 for different virtual environments, and the appropriate database 317 may be accessed based on the virtual environment being utilized. The outline of the object in the virtual environment is compared to outlines of pre-defined objects in the object models database 317 to find an entry corresponding to an object that has a similar outline. The entry in the object models database 317 preferably comprises characteristic information defining characteristics of the corresponding object, e.g., object type, object size, object friend/foe status, etc.

The object identification and location engine 316 retrieves the entry for the matching object model and processes the information to identify the object and its characteristics as well as determine the relative location and distance of the object to the avatar or character of the user. As mentioned above, by knowing the relative size of the object to that of the avatar or character of the user, and the size of the outline in the captured virtual environment data relative to the avatar or character, the distance of the object from the avatar or character of the user in the virtual environment may be calculated as well as the relative location, e.g., to the right, left, center, behind, etc. Thus, the object identification and location engine 316 retrieves information that provides the identity and characteristics of virtual objects in the virtual environment, as well as their relative location and direction to the avatar or character of the user.

This information generated by the object identification and location engine 316 is provided to the echo generation engine 320. The echo generation engine 320 generates echo data for the object based on its identity, characteristics and relative location. Moreover, in cases of data streams with movement of objects, the movement information may be determined by the object identification and location engine 316 based on previous identifications of the location of the object, i.e. identifying changes in location or position of the object. The echo generation engine 320 generates data for outputting an appropriate audio output based on the identity of the object, its characteristics, and relative location.

For example, in one illustrative embodiment, once a virtual object is identified (location and type) a tone is generated specific to that type of object, such as based on an object model matching operation, a lookup operation in an object database, or the like. That tone is generated as a reflected tone pointed directly back at the user from the target object. The integration into the graphics system, e.g., through graphics API or the like, the illustrative embodiments may actually generate the tone as an outward projection from the user's virtual avatar's location and rely on the echolocation device of the illustrative embodiments to calculate the volume/pitch/direction on the emitted sounds echo bounce back. For less integrated implementations, however, such as a screen scraping implementation, the tone may be generated as having originated at the target object's location and pointed directly back towards the user's virtual avatar. The pitch/volume may be calculated based on the distance from the avatar assuming a constant volume pitch was emitted, for example.

In some embodiments, the echolocation functionality of the ELE 310 may be initiated in response to a user inputting an audio trigger input, e.g., a sound that is to be "reflected" back as an echo, via the interface 318. In such cases, the echo generation engine 320 may utilize the input sound from the user as a base sound that is modified based on the identity, characteristics, and relative location of the object that is represented by the "reflected" echo. In some illustrative embodiments, the user may input different audio trigger inputs depending on the desired classification of virtual objects the user wishes to identify. For example, the user may input a first audio input that indicates to the illustrative embodiments that the user wishes to identify objects that are friendly, while the user may input a second audio input that indicates to the illustrative embodiments that the user wishes to identify objects that are foes.

The echo data generated by the echo generation engine 320 is output via echo output engine 314 to the computing device 330, or may be output to the audio output devices, e.g., speakers, 350-354 directly in embodiments where the ELE 310 is integrated into the computing device 330 or in embodiments where the speakers 350-354 are coupled directly to the ELD 305, either wired or wirelessly. The echo output engine 314 or the computing device 330, depending on the embodiment, controls which speakers 350-354 output the echoes corresponding to the echo data so as to output the echo from a speaker physically located relative to the physical location of the user in a similar manner to the relative location of the object to the avatar or character of the user in the virtual environment.

Meanwhile the computing device 330 outputs the representation of the virtual environment 342 via the video output device 340 associated with the computing device 330. It should be appreciated that in some cases, the video output device 340 may not be provided in the embodiment, as visually impaired persons may not have need of a video output device 340.

Figure 4:
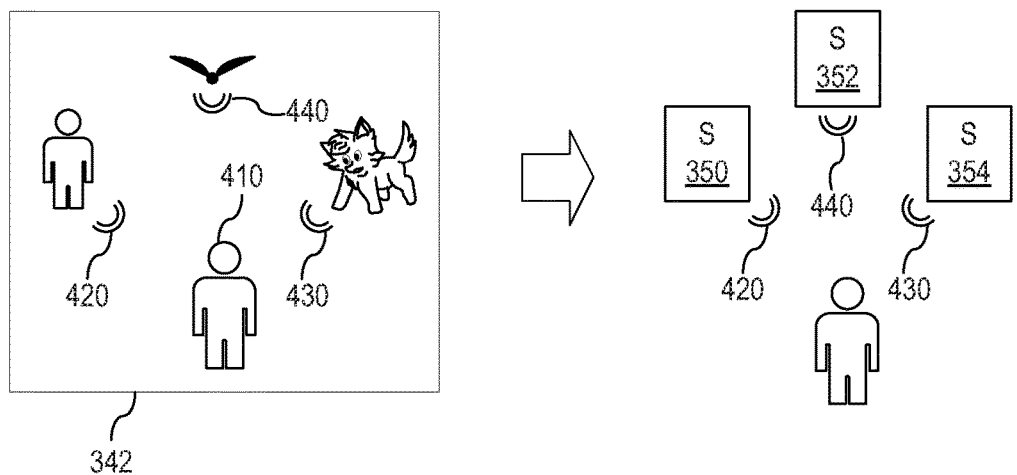
FIG. 4 is an example diagram illustrating the correlation between the locations of virtual objects relative to an avatar and physical locations of speakers relative to a physical user in accordance with one illustrative embodiment.

FIG. 4 is an example diagram illustrating the correlation between the locations of virtual objects relative to an avatar and physical locations of speakers relative to a physical user in accordance with one illustrative embodiment. The virtual environment 342 comprises an avatar or character 410 that represents the user in the virtual environment 342, and a plurality of objects 420-440 representing, in this case, other virtual entities generated as part of the virtual environment 342. Object 420 is to the left front of the avatar 410, object 440 is to the front-above the avatar 410, and object 430 is to the right front of the avatar 410.

As shown in FIG. 4, echoes, or "pings", may be output by the speakers 350-354 in the physical location of the user 450 so as to represent the relative virtual locations of the objects 420-440 within the virtual environment 342, but in the physical environment. Thus, as the object 420 is to the left front, a corresponding speaker 350 physically positioned at left front of the user 450 is used to output the echo corresponding to object 420. Similarly, as the object 440 is to the front above, a corresponding speaker 352 physically positioned at the center front of the user 450, and potentially located in an elevated position relative to the user 450, is used to output the echo corresponding to the object 440. Moreover, for object 430 located to the right front, a corresponding speaker 354 physically position at right front of the user 450 is used to output the echo corresponding to the object 430.

It should be appreciated that for simplicity of the explanation, the present description presents scenarios in which the echoes are output from a single speaker, however the illustrative embodiments are not limited to such. To the contrary, in many cases, it may be necessary to utilize a plurality of speakers to output a single echo, such as to represent locations of objects that do not exactly align with the position of the speakers 350-354 in the physical environment. Thus, the echo output engine 314 and/or computing device 330 may determine, based on the echo data generated by the echo generation engine 320, how to control each of the speakers to output the echo so as to represent the corresponding location of the object. The particular characteristics of the echo itself are used to represent other characteristics of the object, e.g., identity or type, friend/foe status, distance, movement, and the like.

Thus, the illustrative embodiments provide mechanisms for generating a virtual audio environment (VAE) by providing echolocation functionality that assists visually impaired persons with understanding the virtual objects present in a virtual environment and their relative locations to the virtual avatar or character representing the user in the virtual environment. The illustrative embodiments provide specifically configured computing devices that operate in conjunction with audio output devices to output echoes to allow echolocation by visually impaired persons where the echoes themselves are specific to the particular characteristics of the virtual objects that they represent.

Figure 5:
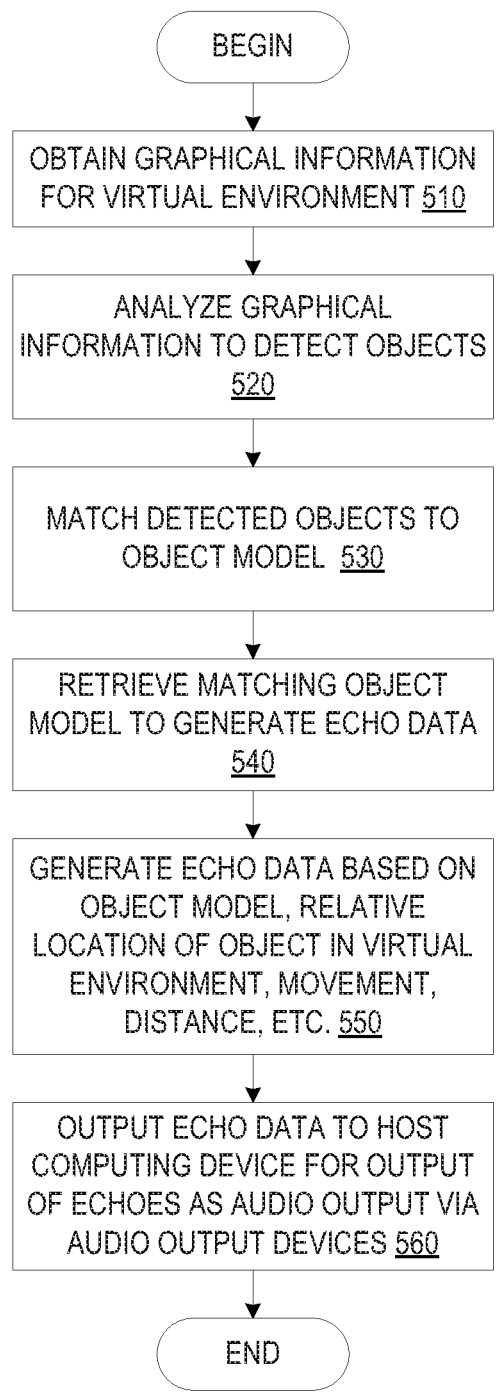
FIG. 5 is a flowchart outlining an example operation of an echolocation device in accordance with one illustrative embodiment.

FIG. 5 is a flowchart outlining an example operation of an echolocation device in accordance with one illustrative embodiment. As shown in FIG. 5, the operation starts by obtaining graphical information for a virtual environment (step 510). As mentioned above, this obtaining of graphical information may take many different forms depending on the particular implementation including, but not limited to, screen scraping technology, direct access of data streams from graphics APIs, or the like. The graphical information is analyzed to identify objects present in the graphical information (step 520). As mentioned above, this analyzing of graphical information to identify objects may take various forms depending on the particular implementation including, but not limited to, edge detection technology that analyzes the pixel information to determine edges of objects based on the color, brightness, or other characteristic differences in pixels of the graphical information.

The detected objects in the graphical information are then matched to pre-defined object models in an object models database (step 530) to identify and retrieve an object model specifying the characteristics of the matching object (step 540). The object model, relative location of object in the virtual environment, movement, distance, and other characteristics of the object are processed to generate echo data defining the audio output (echo) representing the object to be output via an audio output device (step 550). The echo data may specify the tone, pitch, frequency, and particular audio output device(s) that are to be used to output the echo (e.g., front right speaker, left front speaker, center speaker, left rear, right rear, side speakers, etc.). The echo data is output to the host computing device for processing to output the corresponding audio output (echo) via the audio output device(s) specified in the echo data (step 560). The operation then terminates.

While FIG. 5 shows the operation terminating, it should be appreciated that the operation may be repeated as necessary depending on the implementation. For example, if echoes are to be generated each time the position of an object changes or the position of the avatar or character changes, then the operation set forth in FIG. 5 may be repeated when generating the new echoes. Moreover, in an embodiment in which the graphical information is obtained continuously, such as via a data stream from a graphics API or the like, the operation in FIG. 5 may be continuously repeated. Moreover, the operation in FIG. 5 may be performed in parallel for multiple different objects present in the virtual environment.

Thus, the mechanisms of the illustrative embodiments provide an echolocation functionality for users within a virtual environment that emulates echolocation that would occur had the virtual environment been a physical environment. Moreover, in some illustrative embodiments, this echolocation functionality is further embellished with functionality that is available only in virtual environments by being able to represent different characteristics of virtual objects in the characteristics of the echoed sounds that otherwise, in the physical environment, would not necessarily be represented in the echoed sounds, e.g., friend/foe, etc.

Thus, the illustrative embodiments provide the ability to translate a visual world into an audio world. The illustrative embodiments analyze a virtual environment, identifying virtual objects whose presence is to be track spatially, and recreating the equivalent of what an echo-location capable human would experience if these objects were really in that virtual world.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication-based network adapters may also be utilized including, but not limited to, 802.11a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising a memory configured with instructions for execution by a processor of the data processing system to configure the processor to implement an echolocation engine, the method comprising:
   receiving, by the echolocation engine executing on the data processing system, graphical information for a virtual environment;
   analyzing, by the echolocation engine, the graphical information to detect a virtual object present in the virtual environment;
   identifying, by the echolocation engine, one or more first characteristics of the detected virtual object, wherein the one or more first characteristics comprise a relative location of the virtual object to a virtual representation of a user in the virtual environment and a shape identifying characteristic of the virtual object;
   matching, by the echolocation engine, the shape identifying characteristic of the virtual object to an object model in an object database, and retrieving at least one second characteristic of the virtual object, different from the one or more first characteristics, based on the matched object model;
   generating, by the echolocation engine based on the one or more first characteristics and the at least one second characteristic of the virtual object, echo data defining characteristics of an audio output that represents the virtual object in a manner emulating an echo of a sound emitted from the virtual representation of the user in the virtual environment, wherein the characteristics of the audio output comprise an identification of one or more audio output devices to output the audio output based on the relative location of the virtual object to the virtual representation of the user; and
   controlling, by the echolocation engine, output of the audio output by the one or more audio output devices based on the generated echo data.

2. The method of claim 1, wherein the data processing system is a stand-alone device or appliance physically or wirelessly coupled to a computing device that renders the virtual environment, and from which the graphical information is received.

3. The method of claim 2, wherein the computing device that renders the virtual environment is a video game console.

4. The method of claim 1, wherein receiving the graphical information for the virtual environment comprises at least one of performing a screen scraping operation to capture images that are displayed on a display device, or obtaining the graphical information from a graphical application programming interface.

5. The method of claim 1, wherein analyzing the graphical information to detect the virtual object present in the virtual environment comprises performing an edge detection operation on the graphical information to identify one or more edges of the virtual object.

6. The method of claim 1, wherein the at least one second characteristic comprises a friend or foe status of the virtual object relative to the user.

7. The method of claim 1, further comprising:
   receiving an audio input from the user via an audio capture device associated with the echolocation engine, wherein generating echo data defining characteristics of the audio output comprises using the audio input as a basis for the audio output such that the audio output represents a reflection of the audio input from the virtual object.

8. A computer program product comprising a computer readable storage medium having a computer readable program stored therein, wherein the computer readable program, when executed on a data processing system, causes the data processing system to implement an echolocation engine that operates to:
   receive graphical information for a virtual environment;
   analyze the graphical information to detect a virtual object present in the virtual environment;
   identify one or more first characteristics of the detected virtual object, wherein the one or more first characteristics comprise a relative location of the virtual object to a virtual representation of a user in the virtual environment and a shape identifying characteristic of the virtual object;
   match the shape identifying characteristic of the virtual object to an object model in an object database, and retrieve at least one second characteristic of the virtual object, different from the one or more first characteristics, based on the matched object model;
   generate, based on the one or more first characteristics and the at least one second characteristic of the virtual object, echo data defining characteristics of an audio output that represents the virtual object in a manner emulating an echo of a sound emitted from the virtual representation of the user in the virtual environment, wherein the characteristics of the audio output comprise an identification of one or more audio output devices to output the audio output based on the relative location of the virtual object to the virtual representation of the user; and control output of the audio output by the one or more audio output devices based on the generated echo data.

9. The computer program product of claim 8, wherein the data processing system is a stand-alone device or appliance physically or wirelessly coupled to a computing device that renders the virtual environment, and from which the graphical information is received.

10. The computer program product of claim 9, wherein the computing device that renders the virtual environment is a video game console.

11. The computer program product of claim 8, wherein the computer readable program causes the echolocation engine implemented on the data processing system to receive the graphical information for the virtual environment at least by at least one of performing a screen scraping operation to capture images that are displayed on a display device, or obtaining the graphical information from a graphical application programming interface.

12. The computer program product of claim 8, wherein the computer readable program causes the echolocation engine implemented on the data processing system to analyze the graphical information to detect the virtual object present in the virtual environment at least by performing an edge detection operation on the graphical information to identify one or more edges of the virtual object.

13. The computer program product of claim 8, wherein the at least one second characteristic comprises a friend or foe status of the virtual object relative to the user.

14. The computer program product of claim 8, wherein the computer readable program causes the echolocation engine implemented on the data processing system to receive an audio input from the user via an audio capture device associated with the echolocation engine, wherein the computer readable program causes the echolocation engine implemented on the data processing system to generate echo data defining characteristics of the audio output at least by using the audio input as a basis for the audio output such that the audio output represents a reflection of the audio input from the virtual object.

15. An apparatus comprising:
a processor; and
a memory coupled to the processor, wherein the memory comprises instructions which, when executed by the processor, cause the processor to implement an echolocation engine that operates to:
receive graphical information for a virtual environment;
analyze the graphical information to detect a virtual object present in the virtual environment;
identify one or more first characteristics of the detected virtual object, wherein the one or more first characteristics comprise a relative location of the virtual object to a virtual representation of a user in the virtual environment and a shape identifying characteristic of the virtual object;
match the shape identifying characteristic of the virtual object to an object model in an object database, and retrieve at least one second characteristic of the virtual object, different from the one or more first characteristics, based on the matched object model,
generate, based on the one or more first characteristics and the at least one second characteristic of the virtual object, echo data defining characteristics of an audio output that represents the virtual object in a manner emulating an echo of a sound emitted from the virtual representation of the user in the virtual environment, wherein the characteristics of the audio output comprise an identification of one or more audio output devices to output the audio output based on the relative location of the virtual object to the virtual representation of the user; and
control output of the audio output by the one or more audio output devices based on the generated echo data.

16. The method of claim 4, wherein identifying one or more first characteristics of the detected virtual object comprises performing an edge detection operation on the captured image data or graphical information to determine edges associated with objects present in an output of the virtual environment.

17. The method of claim 1, wherein the at least one second characteristic comprises a virtual material of which the virtual object is composed, and wherein generating echo data defining characteristics of an audio output that represents the virtual object further comprises generating echo data representing an echoed audio signal reflected by a virtual object composed of the virtual material.

18. The method of claim 1, wherein matching the one or more first characteristics of the virtual object to an object model in an object database further comprises retrieving, by the echolocation engine based on an identification of the virtual environment, the object database from a plurality of object databases, wherein each object database in the plurality of object databases is associated with a different virtual environment.

19. The method of claim 1, wherein analyzing the graphical information to detect a virtual object present in the virtual environment comprises:
analyzing the graphical information to detect a first subset of virtual objects corresponding to background virtual objects for which echolocation is not to be performed; and
analyzing the graphical information to detect a second subset of virtual objects corresponding to important virtual objects for which echolocation is to be performed, wherein the virtual object is a virtual object present in the second subset of virtual objects.

20. The method of claim 7, further comprising:
determining, by the echolocation engine, whether the audio input from the user is a first audio input indicating a command by the user to identify only friendly virtual objects in the virtual environment, or a second audio input indicating a command by the user to identify only foe virtual objects in the virtual environment, wherein analyzing the graphical information to detect a virtual object present in the virtual environment comprises identifying the virtual object from a subset of virtual objects present in the virtual environment that are either friend virtual objects or foe virtual objects based on the user input.

* * * * *